US005469874A

United States Patent [19]

Meyer et al.

[11] Patent Number: 5,469,874

[45] Date of Patent: Nov. 28, 1995

[54] APPARATUS AND METHOD FOR PREFORMING DENTAL FLOSSING

[75] Inventors: Stuart L. Meyer, Chicago, Ill.; Eric S. Meyer, Gaithersburg, Md.; David M. Meyer, Palo Alto, Calif.; Jonathan I. Meyer, Shake-Heights, Ohio

[73] Assignee: Televideo Consultants, Inc., Evanston, Ill.

[21] Appl. No.: 201,344

[22] Filed: Feb. 24, 1994

[51] Int. Cl.$^{6}$ .................... A61C 15/00

[52] U.S. Cl. .................... 132/323; 132/324

[58] Field of Search .................... 132/323, 324, 132/325, 326, 327

[56] References Cited

U.S. PATENT DOCUMENTS

| | | | |
|---|---|---|---|
| D. 251,074 | 2/1979 | Schiff | D28/64 |
| 2,607,357 | 8/1952 | Talcott | 132/325 |
| 2,650,598 | 9/1953 | Rodesci | 132/91 |
| 3,393,687 | 7/1968 | Whitman | 132/323 |
| 3,799,177 | 3/1974 | Bragg | 132/326 |
| 4,050,470 | 9/1977 | Miller | 132/323 |
| 4,304,246 | 12/1981 | Yafai | 132/91 |
| 4,519,408 | 5/1985 | Charatan | 132/89 |
| 4,982,752 | 1/1991 | Rodriguez | 132/327 |
| 5,123,432 | 6/1992 | Wyss | 132/323 |
| 5,224,501 | 6/1993 | McKenzie | 132/323 |

FOREIGN PATENT DOCUMENTS

| | | | |
|---|---|---|---|
| 681686 | 5/1993 | Switzerland | 132/324 |

*Primary Examiner*—John G. Weiss

*Attorney, Agent, or Firm*—Willian Brinks Hofer Gilson & Lione

[57] ABSTRACT

A flossing apparatus and method of flossing. The flossing apparatus comprises a pair of separate and distinct flossing handles which are interconnected by a loop of dental floss. The loop is formed from a length of dental floss and includes a working segment of floss which interconnects corresponding free ends of the handles, a control segment which interconnects the handles at points displaced from the free ends, and a pair of side segments which run along corresponding handles between respective ends of the working and control segments. The handles are free to move on all axes relative to each other, restrained only by the dimensions of the loop. They are also free to move relative to the loop. The flossing handles are used by manipulating them separately to achieve any optimum working floss segment length and angular relationship between the handles for the particular flossing operation contemplated.

8 Claims, 4 Drawing Sheets

230 236 220 210 231 221 237 271 217 261 272 262 256 255

230
231
271
261
256
236
237
217
220
262
210
221
272
255

130
139
131
156
136
137
135
120
138
115
121
110
155

V WORKING
V A
V B
V CONTROL

4
X
3
Y
Z
2

APPARATUS AND METHOD FOR PREFORMING DENTAL FLOSSING

FIELD OF THE INVENTION

This invention relates generally to dental hygiene. It relates particularly to dental flossing.

BACKGROUND OF THE INVENTION

It has long been known in the field of dental hygiene that it is important to remove food particles, tartar, and plaque from the teeth at least once a day. The removal of such dental contaminants may be accomplished by various means such as by brushing, water spray or the use of dental floss.

Dental floss is conventionally held in the hands and manipulated by the fingers. The floss is inserted between two adjacent teeth, or looped partially around a single tooth and pulled, or pushed back and forth against the tooth to remove the food particles, tartar and plaque. This procedure requires a certain amount of manual dexterity and also requires the flosser to insert his or her fingers into the mouth.

A variety of mechanical devices have been developed to aid in the use of dental floss. Among these are devices consisting of a forked or U-shaped handle. In these devices a length of dental floss is tautly stretched between the two tines of a device. The device is manipulated from outside the mouth so as to draw the dental floss up and down against the surface of the tooth to be cleaned. Examples of such devices are found in Schiff U.S. Pat. No. Des. 251,074 and the Yafai U.S. Pat. No. 4,304,246. In the latter, the floss is in the form of a loop which is stretched around the device.

In another flossing device, illustrated and described in the Wyss U.S. Pat. No. 5,123,432, parallel handles have a floss loop extending through them and interconnected across opposite ends. The handles are spaced at their mid-points by a spacer member which forms a fulcrum. The handles are manipulated by squeezing them at one end so that they pivot in a plane about the fulcrum and draw the floss tight at one end (the flossing end). In lieu of the spacer member illustrated, the handles may be manipulated in the same manner about a fulcrum formed by the flosser's finger.

In yet another flossing device, illustrated and described in the Bragg U.S. Pat. No. 3,799,177, the use of two separate handles is shown. A length of floss is stretched between the corresponding working ends of the handles and flossing accomplished by manipulating the other ends separately.

SUMMARY OF THE INVENTION

An object is to provide an improved apparatus for dental flossing.

Another object is to provide an improved flossing apparatus comprising a pair of independently controlled flossing handles which are interconnected only by a loop of floss.

Yet another object is to provide an improved dental flossing apparatus wherein segments of the floss loop which interconnect the handles are lengthened and shortened at will and in an endless variety of ways by manipulating the handles independently of each other.

Another object is to provide a flossing apparatus which can be effectively used while inserting only a minimal amount of the apparatus into the mouth.

Still another object is to provide a flossing apparatus which can readily be adapted to incorporate a lengthy store of floss.

A further object provides a flossing apparatus which is simple and inexpensive to manufacture.

Another object of the present invention is to provide a new and improved method of dental flossing.

The foregoing and other objects are realized in accord with the present invention by providing a flossing apparatus comprising a pair of separate and distinct flossing handles which are interconnected by a loop of dental floss. By a closed loop it is meant that the length of dental floss which forms the loop is unbroken or has opposite ends which cross in such a way that the loop cannot be entered without being broken. The closed loop is formed from a length of dental floss and includes a working segment of floss which interconnects corresponding free ends of the handles, a control segment which interconnects the handles at points displaced from the free ends, and a pair of side segments which run along corresponding handles between respective ends of the working and control segments. The handles are free to move on all axes relative to each other, restrained only by the dimensions of the loop. They are also free to move relative to the loop.

In one embodiment of the flossing apparatus, the handles are of identical length. The floss loop passes through connecting apertures at opposite ends of each handle. Free ends of the length of floss which form the loop are tied together or otherwise interconnected in the control segment (or side segments) of the loop so that the length of floss is effectively continuous.

In another embodiment of the flossing apparatus, the handles are of identical length but are considerably longer than those in the previously described embodiment. The handles each extend beyond the point where the control segment of the floss loop interconnects with handles, providing handle extensions, if you will.

In a modification of the other embodiment, the single, continuous loop is replaced by a floss store mounted on one of the handle extensions. A closed loop is then effectively formed between the handles by passing it through the connecting apertures twice to form a control segment—in a manner hereinafter explained. This forms what is called here a "virtual loop", i.e. a loop which is closed but which is comprised of a length of floss whose free ends cross in the aforedescribed manner. The loop is closed only by virtue of its opposite ends passing through apertures or other control means in a common support member. The floss is then anchored adjacent the floss store, and the free end of the floss is anchored to the other handle extension.

In this modification, a variety of floss storing, cutting and anchoring mechanisms may be employed. For example, the floss store may be simply formed around a cleat. In the alternative, a container of floss may be mounted on one handle extension.

In yet another embodiment of the flossing apparatus, longer handles, i.e., handles which include extensions beyond the control segment of the floss loop are employed. The floss loop is continued to the free ends of the extensions where it passes through apertures thereon to form another loop. The result is a double floss loop or figure eight loop, i.e., both virtual loops (two of them) and a continuous one. This embodiment may be used advantageously with one hand; for example, by a handicapped flosser.

In the method of the invention the flossing handles are normally used by manipulating them separately to achieve any optimum working floss segment length and angular relationship between the handles for the particular flossing operation contemplated. Only a short length of the apparatus is inserted in the mouth. The flosser applies pressure to the control segment of the floss, to the handles or to both handles and control segment to control pressure on the tooth being flossed.

BRIEF DESCRIPTION OF THE DRAWINGS

The invention, including its construction and method of operation, as well as additional advantages thereof, is illustrated more or less diagrammatically in the drawings, in which.

DESCRIPTION OF THE PREFERRED EMBODIMENTS

Figure 1:
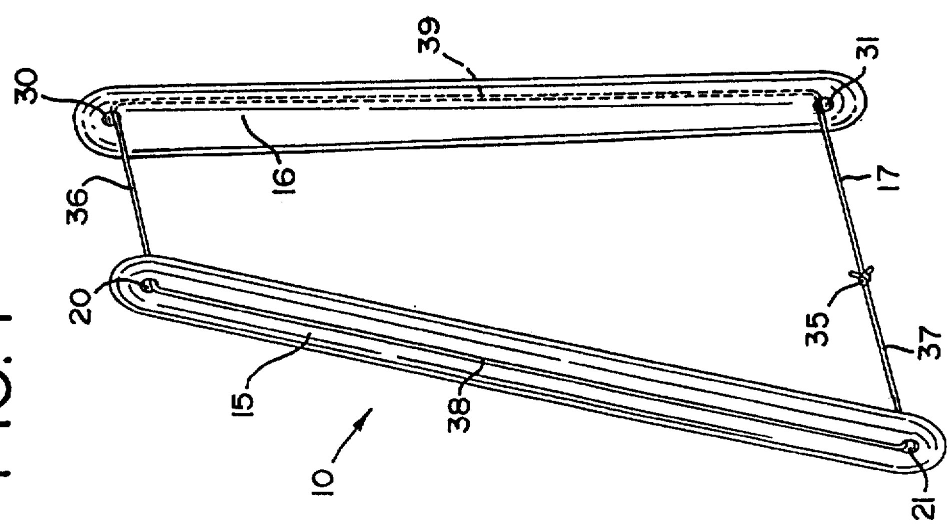
FIG. 1 is a perspective view of a first form of flossing apparatus embodying features of the present invention.

Referring now to the drawings, and particularly to FIG. 1, a flossing apparatus embodying a first form of the present invention is seen generally at 10. The apparatus 10 comprises a pair of identical flossing handles 15 and 16 interconnected by a loop continuous 17 of conventional dental floss.

The handles 15 and 16 are each about three inches long. Each is preferably formed of molded plastic, although wood or any one of many different materials could be used. The handles 15 and 16 shown each have a circular cross-section, with a diameter of about one-quarter inch. The dimensions and shapes described are not critical to the invention, however, and may be varied without obvious limits.

Small apertures 20 and 21 are formed transversely through opposite ends of the handle 15. Identical apertures 30 and 31 are formed through corresponding opposite ends of the handle 16.

A piece of dental floss nine and one-half inches long is threaded through the apertures 21, 20, 30 and 31, and its free ends are tied together at a knot 35 to form the loop 17. With the apparatus 10 assembled in this way, the loop 17 is effectively divided into four segments, a floss working segment 36 between the apertures 20 and 30, a control segment 37 between the apertures 21 and 31, and a pair of side segments 38 and 39 paralleling corresponding handles 15 and 16.

The apparatus 10 is illustrated in FIG. 1 in its normal operating set-up. The handles 15 and 16 are inclined toward each other at the handle ends which carry the working segment 36 of the loop 17 between them. They are inclined in such a way that the working segment 36 is between one-quarter inch and one inch long. The opposite ends of the handles 15 and 16 have the control segment 37 of the loop 17 between them. The control segment 37 is then between about three and one-quarter inches and two and one-half inches long. In this operating set-up, the handles 15 and 16 would also normally be arranged so as to be non-coplanar.

Figure 2:
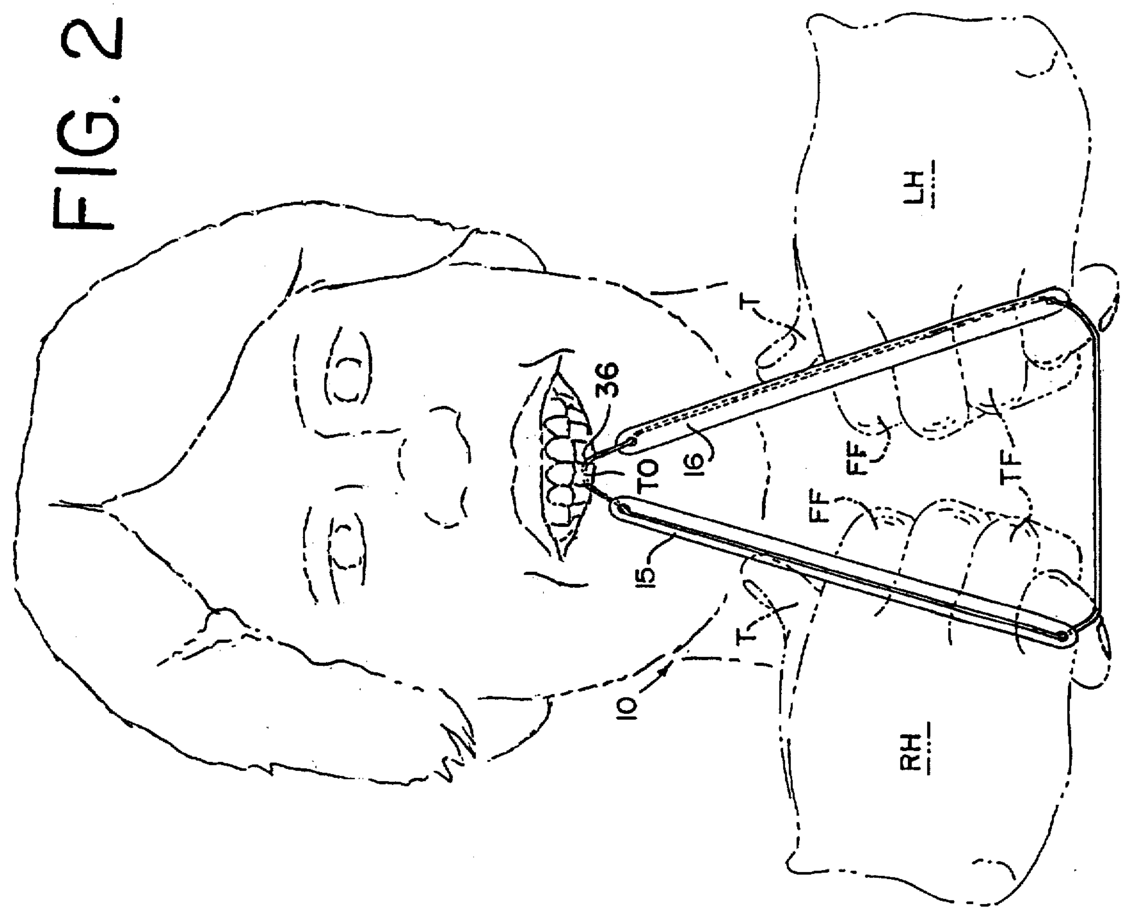
FIG. 2 is another perspective view of the first form of flossing apparatus, illustrating the method of the invention employed in properly flossing with the apparatus.

Referring now to FIG. 2, the flossing apparatus 10 is shown in the hands RH and LH of the flosser as it is used according to the method of the invention. The handles 15 and 16 are grasped between the thumb T and forefinger FF of the right hand RH and the left hand LH, respectively. The third finger TF of one or both hands is then placed over or under the control segment 37 of the floss loop 17.

The flosser then inserts the working segment 36 of the floss loop 17 into position in front of or behind a tooth, or around a tooth (as shown). The handles 15 and 16 can be disposed in any angular relationship to each other in order to place the working segment 36 in the most advantageous position for each flossing operation, and the operation performed by changing that angular relationship or while maintaining it. Flossing pressure is applied by the third finger(s) TF of the flosser's hands pushing or pulling on the control segment 37 of the floss loop 17. In the alternative, this flossing pressure can also be maintained by tilting (pushing or pulling) the handles away from each other at the control segment.

In geometry terms, the vectors defined by the two handles 15 and 16 can be deployed in such fashion as to be linearly independent of each other. That is, the handles 15 and 16 can be deployed in space in such fashion that their vectors never meet, if extended.; even when they are not parallel. The loop 17 that is formed by floss passing through the apertures in the handles can, in fact, be non-planar. This confers more degrees of freedom on the handles 15 and 16 and the loop segment 36 at the business end of the handles. This is very different from prior art flossing implements. They are not only coplanar, usually being configured in a "fork" geometry, but the plane of the floss segment and the plane of the arms or handles are normally coupled rigidly.

Figure 3A:
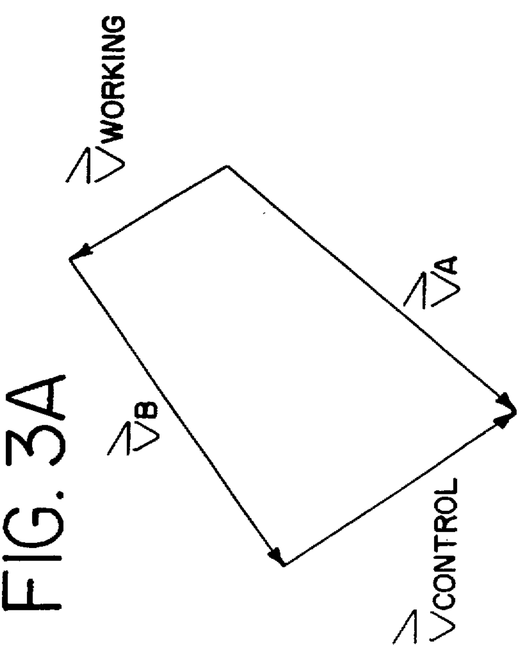
FIG. 3A is a vector diagram illustrating certain features of the invention.
Figure 3B:
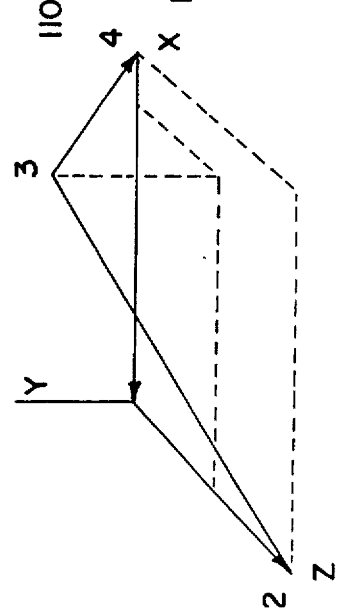
FIG. 3B is an illustration of the vector diagram of FIG. 3A on a three-axis (X, Y, Z) graph.

The mathematical expression of this relationship in the present invention illustrates the distinction between the present invention and the prior art. Referring now to the illustration of FIG. 3, consider one handle 15 to be a directed line segment called VECTOR, $\vec{V}_A$, where the other handle 16 is a directed line segment called VECTOR, $\vec{V}_B$. The working segment 36 of the floss is also a directed line segment called VECTOR, $\vec{V}_{WORKING}$, where the size of the segment can vary. The control segment 37 of the floss is not independent, since $\vec{V}_{CONTROL\ SEGMENT}$, is defined by the relation:

$$\vec{V}_{CONTROL\ SEGMENT}=\vec{V}_A-\vec{V}_B-\vec{V}_{WORKING\ SEGMENT}$$

(this, of course, is why the $\vec{V}_{WORKING\ SEGMENT}$ is determined by $\vec{V}_A$, $\vec{V}_B$ and $\vec{V}_{CONTROL\ SEGMENT}$). The coplanarity (linear dependence) relation is thus defined by $[\vec{V}_A\vec{V}_B]\bullet\vec{V}_{WORKING\ SEGMENT}=0$, where the vector operators indicate VEC- TOR CROSS PRODUCT and VECTOR DOT PRODUCT, respectively. The NON-COPLANARITY CONDITION, which is a feature of the present invention, is defined by [$\vec{V}_A \times \vec{V}_B$]$\bullet \vec{V}_{working\ segment} \neq 0$.

Why is this relationship important?. The object of using a tool to deploy floss segments within the mouth is to avoid having to distend the mouth unduly, or to trigger a gag reflex, or to insert non-hygienic fingers, or to insert fingers encased in latex, which has the disadvantage of tasting bad, smelling unpleasant and triggering allergic reactions to latex. This means that the floss segment should be deployable without having to change the orientation of the handles, point for point. The degrees of freedom inherent in the present invention allow the apparatus to change relatively little outside the mouth while permitting complete flexibility in deploying the working floss segment. There should be as little of the apparatus in the mouth as possible, aside from the floss segment.

In the present invention, the working floss segment is variable in length, as well as orientatable in space. The apparatus allows the working floss segment to be long or short, at will. It also allows the floss working segment to be taut, by itself, or pulled around a tooth or pushed against a tooth. That is, the floss working segment can be put under tension in either a line segment (when inserting between teeth) or in a curvilinear arc convex to the front of the mouth (when pushing against the tooth) or concave to the front of the mouth when pulling against a tooth.

Figure 4:
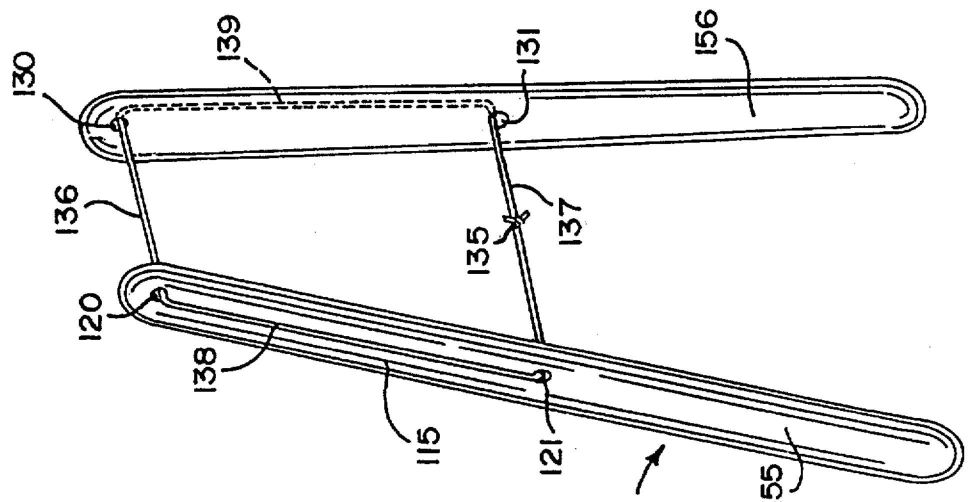
FIG. 4 is a view, similar to FIG. 1, illustrating a second form of flossing apparatus embodying features of the present invention.

Referring now to FIG. 4, a flossing apparatus embodying a second form of the present invention is seen generally at 110. The apparatus 110 is, in many respects, identical in construction to the flossing apparatus 10 hereinbefore discussed. To the extent that components are identical, corresponding reference numerals, plus one-hundred digits, are used.

As seen in FIG. 4 a floss loop 117 is mounted on a pair of identical flossing handles 115 and 116 by passing it through apertures 120 and 130 on corresponding ends of the handles and apertures 121 and 131 spaced about three inches from corresponding apertures 120 and 130. The loop 117 is knotted at 135 and includes a working segment 136, an operating segment 137 and side segments 138 and 139.

Unlike the apparatus 10, however, the handles 115 and 116 have handle extensions 155 and 156 below the apertures 121 and 131. These extensions 155 and 156 are each approximately four inches long, making the handles 115, 155 and 116, 156 each about seven inches long.

This configuration of the flossing apparatus 110 permits the flosser to grip the handle extensions 155 and 156 and manipulate the working segment 136 of the floss from a point further removed from the mouth. All of the advantages of the apparatus 10 are retained.

Figure 5:
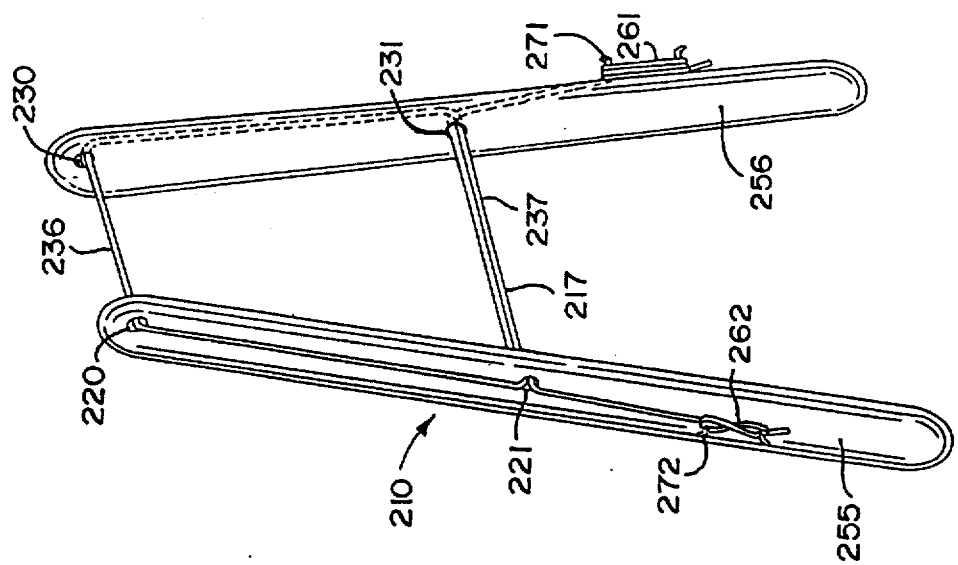
FIG. 5 is a view, similar to FIG. 3, illustrating a modification of the second form of flossing apparatus.

Referring now to FIG. 5, a modification of the second form of flossing apparatus is illustrated at 210. The apparatus 210 is, in most respects, identical to the flossing apparatus 110 hereinbefore discussed. To the extent that components are identical, corresponding reference numerals, plus one-hundred digits, are used.

As seen in FIG. 5, rather than being knotted at opposite free ends to form a loop, the loop 217 is formed by passing opposite ends 261 and 262 of the piece of floss through both apertures 221 and 231, in opposite directions. One end 261 is then wrapped numerous times around a cleat 271 on the handle extension 256 to form an anchored store of floss. The other end 262 is wrapped around a similar cleat 272 on the handle extension 255 to anchor it there.

The second form of flossing apparatus 210 is employed using the same method described with relation to the apparatus 110. As will be seen, however, it is not necessary to remove and replace the floss loop 217 after use. Floss is simply unwound from the store 261 on the cleat 271 for an inch or two and pulled through the apertures 231, 221, 220, 230, 231 and 221, in that order. The floss is then anchored again at the cleat 272, after which the excess can be cut off. This permits a very frugal use of floss since, for a single user, only one inch of new floss is needed for each "freshening". Alternatively, a completely pristine nine to ten inches of floss can be withdrawn for a new use and the excess discarded. An unused working segment 236 of floss is then in position.

Figure 6:
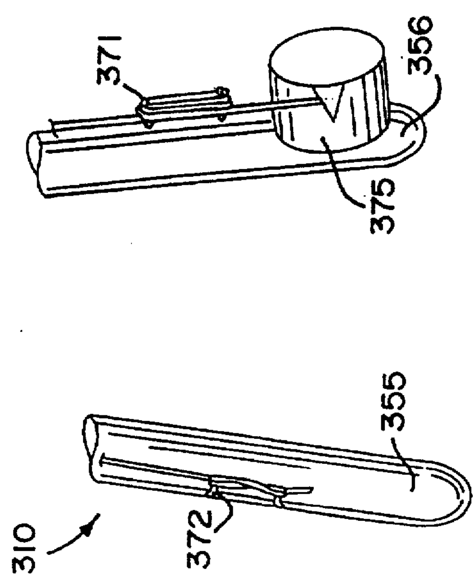
FIG. 6 is a view, similar to FIG. 3, illustrating another modification of the second form of flossing apparatus.

Referring now to FIG. 6, another modification of the second form of flossing apparatus is illustrated at 310 (only the handle extensions 355 and 356, corresponding to the extensions 255 and 256 in FIG. 5, are shown). In the apparatus 310, a mounting receptacle 375 is affixed to the handle extension 356 and, in this receptacle, a standard small-size floss capsule 376 is removable mounted.

Floss is drawn from the capsule 376 and threaded through handle apertures in the manner illustrated in FIG. 5. When sufficient floss to reach and go well past an anchor cleat 372 on the handle extension 355 has been reached, the floss at the capsule 376 is placed under the conventional anchor cleat 371 associated with it. The free end is then anchored onto the cleat 372.

With regard to the aforedescribed modifications of the second embodiment, a wide variety of floss storage and anchoring mechanisms could be used. In addition, where such storage capability is provided, a floss cutting mechanism on the handle extension opposite the storage mechanism is preferably incorporated.

Figure 7:
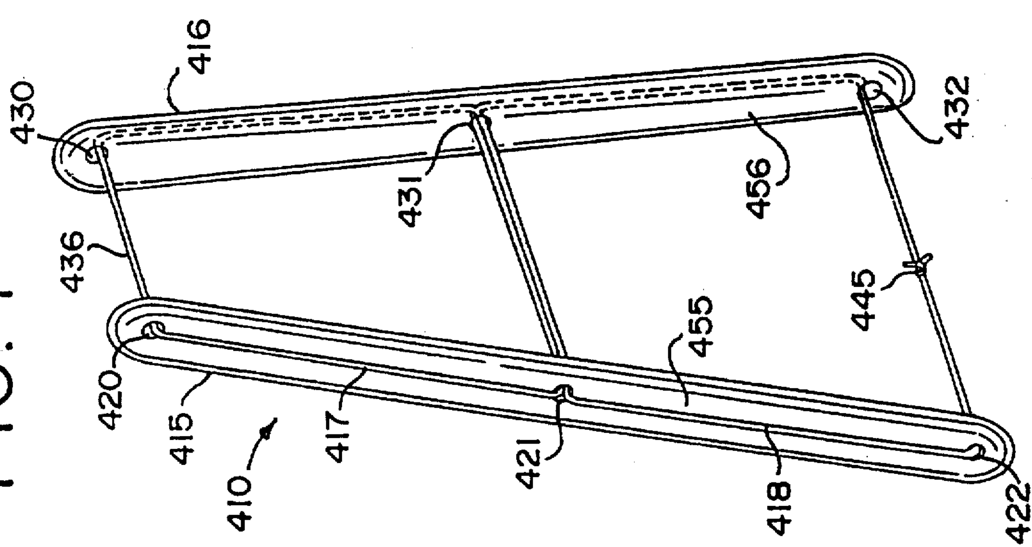
FIG. 7 is a view, similar to FIG. 1, illustrating a third form of flossing apparatus embodying features of the present invention.

Referring now to FIG. 7, a flossing apparatus embodying a third form of the present invention is seen generally at 410. The apparatus 410 is, in many respects, identical in construction to the flossing apparatus 110 hereinbefore discussed. To the extent that components are identical, corresponding reference numerals, plus three-hundred digits, are used!

As seen in FIG. 7, the floss virtual loop 417 is only part of a larger, closed double-loop 417, 418. The lower loop 418 is formed by crossing the ends of the length of floss through the apertures 421 and 431 and extending those ends downwardly along the handle extensions 455 and 456 to apertures 422 and 432 in corresponding extensions. The ends of the floss segment are then passed inwardly through the apertures 422 and 432 and tied together at a know 445.

With this configuration apparatus 410, flossing can be done easily with one hand. The handle extensions 455 and 456 are gripped between fingers of one hand, somewhat like chopsticks, and the position, length and pressure applied by the floss working segment 436 controlled in this way.

Figure 8:
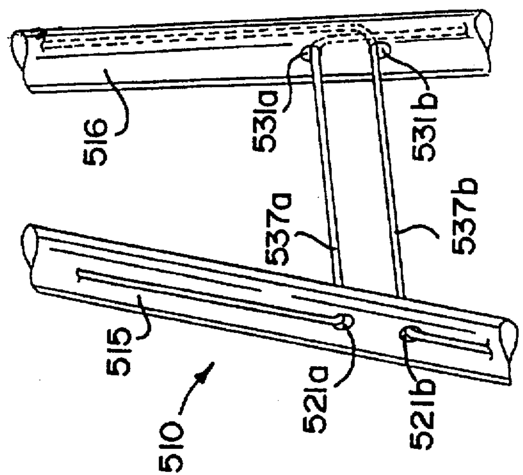
FIG. 8 is a perspective view of a variation on the flossing apparatuses shown in FIGS. 5, 6 and 7.

Referring now to FIG. 8, a variation of the apparatuses 210, 310 and 410 hereinbefore discussed is seen in the flossing apparatus 510 (partially shown). It amounts to the creation of a spaced pair of apertures 521*a*, 521*b* and 531*a*, 531*b* in each of the handles 515 and 516. In forming the control segment 537 of the floss, the floss ends are threaded in opposite directions through the upper set of apertures 521*a*, 531*a* and the lower set 521*b*, 531*b*, respectively. Upper and lower floss control segments 537*a* and 537*b* are, thus, formed.

Figure 9:
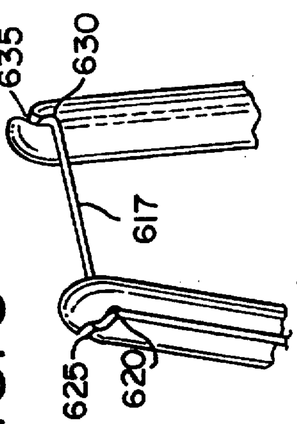
FIG. 9 is a perspective view of a variation on the flossing apparatuses shown in all preceding FIGURES.

Referring now to FIG. 9, a variation of all the apparatuses hereinbefore discussed is seen in the flossing apparatus 610 (partially shown). It has slots 625 and 635 leading into corresponding apertures 620 and 630 through the handles 615 and 616. The slots 625 and 626 are duplicated adjacent corresponding other apertures through the handles (not shown) at their opposite ends. This slot construction permits preformed or pretied loops of floss 617 to be mounted on the handles by sliding them through corresponding slots into related apertures.

Figure 10:
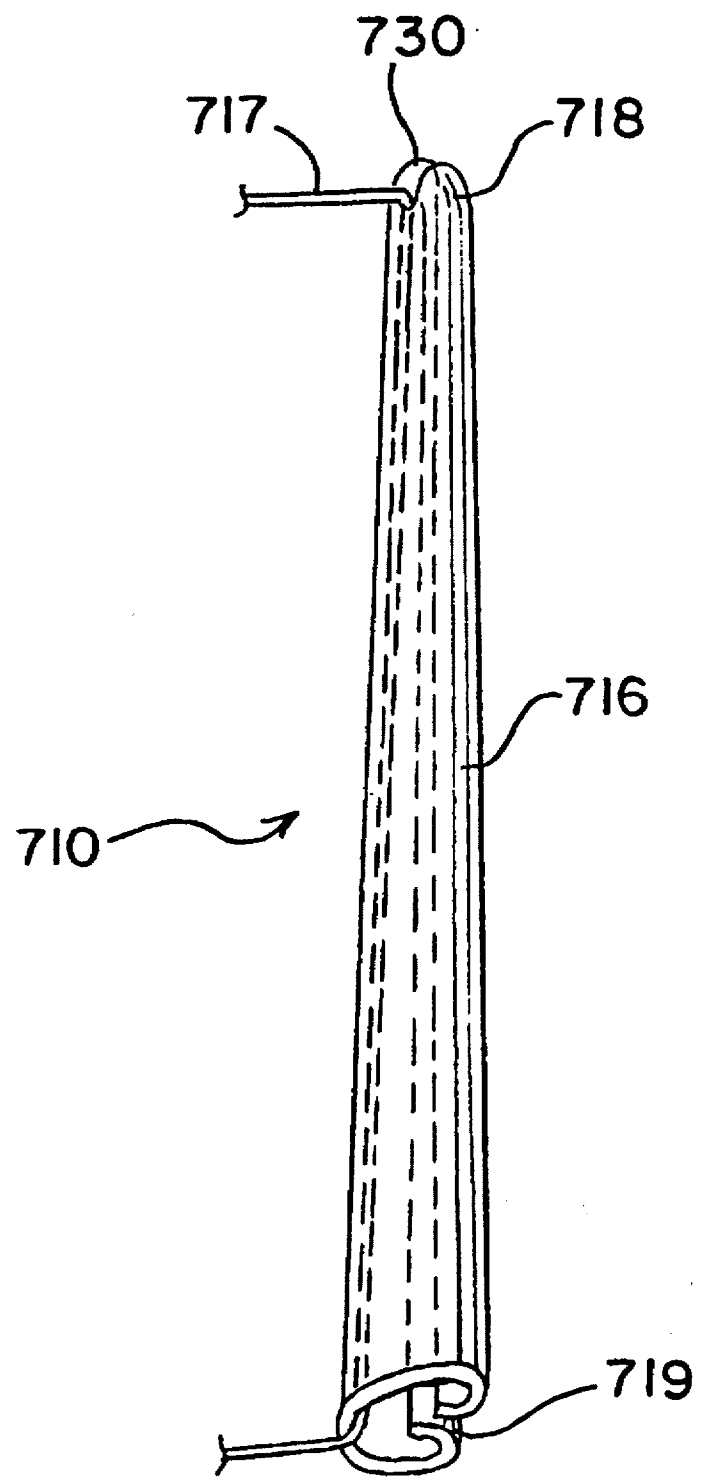
FIG. 10 is a perspective view of another variation of the flossing apparatuses shown.

Referring now to FIG. 10, another variation of apparatuses hereinbefore discussed is seen in the flossing apparatus 710 (partially shown). It comprises a pair of identical handles, but only one is shown, at 716. The handles are each formed with a bullet-shaped tip 718 at its working end. As seen at the opposite (lower) end in FIG. 10, each handle 716 is formed so that a slot 719 extends along its length, with inwardly curled edges 723 of the handle forming the slot. The slot 719 extends across the top of the tip 718 to form an aperture 730 in the tip for the floss 717. This construction also permits preformed or pretied loops of floss to be easily mounted and retained.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

We claim:

1. An apparatus for dental flossing comprising:

a) first and second elongated flossing handles;

b) a length of dental floss having opposite ends;

c) each of said flossing handles having one aperture adjacent a corresponding free end and said opposite ends of said length of dental floss passing through said one apertures to create a working segment of floss between said free ends;

d) each of said flossing handles also having at least one other aperture spaced a predetermined distance from a corresponding one aperture;

e) said opposite ends of said length of dental floss passing through one of said other apertures in each of said handles so as to form a virtual loop including a control segment of floss which is between said handles at said predetermined distance from said one apertures in said handles;

f) each of said flossing handles also having a handle extension which elongates the corresponding handle opposite said other apertures from said working segment of floss; and g) an anchoring mechanism on each of said extensions;

h) said opposite ends of said length of floss each being anchored by an anchoring mechanism.

2. The apparatus of claim 1 further comprising:

a) at least one of said ends of floss being extended so that a substantial length of floss is anchored;

b) said substantial length of floss forming a floss store from which floss can be withdrawn and pulled through said apertures to replace said working segment of the floss.

3. The apparatus of claim 1 further comprising:

a) said floss store being contained in a floss container which is mounted on the corresponding handle extension.

4. The apparatus of claim 3 further comprising:

a) said floss container being readily removable from a mounting structure on the corresponding handle extension.

5. An apparatus for dental flossing comprising:

a) first and second elongated flossing handles having corresponding, opposite free ends;

b) a length of dental floss having opposite ends;

c) each of said flossing handles having one aperture adjacent a corresponding free end of said handles and said opposite ends of said length of dental floss passing through said one apertures to create a working segment of floss between said free ends;

d) each of said flossing handles also having at least one other aperture spaced a predetermined distance from a corresponding one aperture;

e) said opposite ends of said length of dental floss passing through one of said other apertures in each of said handles so as to form a virtual loop including a control segment of floss which is between said handles at said predetermined distance from said one apertures in said handles;

f) said handles always being physically unconnected except for said floss loop so that vectors defined by the handles are linearly independent of each other and the handles can be deployed in space in such a fashion that the vectors are not necessarily in the same plane;

g) each of said flossing handles also having a handle extension which elongates the corresponding handle opposite said other apertures from said working segment of floss; and h) anchoring means;

i) said opposite ends of said length of floss being anchored by said anchoring means;

j) said length of dental floss being movable linearly on each of said handles to permit different segments of said length of dental floss to function as said working segment;

k) manipulation of the handles with both hands permitting substantially unlimited variation in orientation of said handles independently relative to each other except for any restraint imposed by said loop and control of said working segment with said manipulation.

6. The apparatus of claim 5 further comprising:

a) said apertures being formed transversely through said handles.

7. A method of performing dental flossing, comprising the steps of:

a) providing two, separate flossing handles which are connected by a loop of dental floss in a manner which permits the handles to move on all axes relative to each other but are otherwise unconnected;

b) gripping one handle in the fingers of one hand and the other handle in the fingers of the other hand and positioning a working segment of the floss loop, which extends between corresponding one ends of the handles, into the flosser's mouth against the side of a tooth to be flossed;

c) exerting outwardly directed pressure with the fingers on a control segment of the floss extending between the handles and spaced from said working segment and on the handles so as to tension said working segment against the side of the tooth; and d) manipulating the handles independently relative to each other except for any constraint imposed by the length of said loop so as to permit substantially unlimited orientation and control of said working segment with said manipulation.

8. An apparatus for dental flossing of teeth comprising:

a) first and second elongated flossing handles having corresponding, opposite free ends; and b) a length of dental floss forming a loop connected to each of said handles;

c) said loop of dental floss including a working segment between said handles at one corresponding pair of free ends of said handles and a control segment between said handles at points removed from said one corresponding pair of free ends;

d) each of said flossing handles having one aperture formed thereon adjacent a corresponding one free end of the handle and said loop of dental floss extending through said one apertures;

e) said working segment disposed between said one apertures;

f) each of said flossing handles also having another aperture formed thereon and spaced a predetermined distance from said one aperture in the same handle and said loop of dental floss extending through said other apertures;

g) said control segment disposed between said other apertures;

h) said loop being a virtual loop formed by a length of dental floss having free, opposite ends;

i) each of the free ends of said length of dental floss extending through another aperture in each of said flossing handles;

j) said handles always being physically unconnected except for said floss loop so that vectors defined by the handles are linearly independent of each other and the handles are deployable in space so that the vectors are not necessarily in the same plane;

k) said length of dental floss being movable linearly on each of said handles to permit different segments of said length of dental floss to function as said working segment;

l) manipulation of the handles separately with the fingers of each hand to spread the handles apart, and orient the handles independently of each other except for any constraint imposed by the length of the loop, permitting the loop to be made taut and pressure to be exerted against a tooth by the working segment while pressure is exerted on the control segment by the fingers.

* * * * *

UNITED STATES PATENT AND TRADEMARK OFFICE

CERTIFICATE OF CORRECTION

PATENT NO. : 5,469,874

DATED : November 28, 1995

INVENTOR(S) : Stuart L. Meyer et al.

It is certified that error appears in the above-indentified patent and that said Letters Patent is hereby corrected as shown below:

On the Title Page , Item [54]

In column 1, line 2, delete "PREFORMING" and substitute --PERFORMING--.

In column 1, line 6, delete "Shake-Heights" and substitute --Shaker-Heights--.

In column 1, line 2, delete "PREFORMING" and substitute --PERFORMING--.

In column 4, line 66, delete the following:

"$[\vec{V}_A \vec{V}_B] \bullet$"

and substitute the following:

--$[\vec{V}_A \times \vec{V}_B] \bullet$--.

UNITED STATES PATENT AND TRADEMARK OFFICE

CERTIFICATE OF CORRECTION

PATENT NO. : 5,469,874

DATED : November 28, 1995

INVENTOR(S) : Stuart L. Meyer et al.

It is certified that error appears in the above-indentified patent and that said Letters Patent is hereby corrected as shown below:

In column 5, line 15, delete "outside" and substitute --inside--.

Signed and Sealed this

Tenth Day of December, 1996

Attest:

BRUCE LEHMAN

*Attesting Officer* *Commissioner of Patents and Trademarks*